(12) United States Patent
Obrzut

(10) Patent No.: US 11,160,516 B2
(45) Date of Patent: Nov. 2, 2021

(54) COMPRESSIVE SENSING ABSORBER FOR BREAST IMAGING

(71) Applicant: The Regents of the University of California, Oakland, CA (US)

(72) Inventor: Sebastian Obrzut, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 97 days.

(21) Appl. No.: 16/599,022

(22) Filed: Oct. 10, 2019

(65) Prior Publication Data

US 2020/0113529 A1    Apr. 16, 2020

Related U.S. Application Data

(60) Provisional application No. 62/744,566, filed on Oct. 11, 2018.

(51) Int. Cl.
| | | |
|---|---|---|
| A61B 6/03 | (2006.01) |
| A61B 6/04 | (2006.01) |
| G01T 1/164 | (2006.01) |
| G01T 1/20 | (2006.01) |
| A61B 6/00 | (2006.01) |

(52) U.S. Cl.
CPC ............ *A61B 6/037* (2013.01); *A61B 6/0414* (2013.01); *A61B 6/4258* (2013.01); *A61B 6/4291* (2013.01); *A61B 6/502* (2013.01); *A61B 6/5205* (2013.01); *A61B 6/582* (2013.01); *G01T 1/1648* (2013.01); *G01T 1/2018* (2013.01)

(58) Field of Classification Search
None
See application file for complete search history.

(56) References Cited

U.S. PATENT DOCUMENTS

3,348,319 A * 10/1967 Harrison .............. G09B 23/286
                                                        434/219
4,286,168 A *  8/1981 Carr .......................... G21K 1/10
                                                        250/505.1

(Continued)

OTHER PUBLICATIONS

American Cancer Society. Cancer Facts & Figures 2017. Atlanta.
(Continued)

*Primary Examiner* — Thomas R Artman
(74) *Attorney, Agent, or Firm* — Perkins Coie LLP

(57) ABSTRACT

Disclosed is a breast imaging system including a compressive sensing absorber (CSA) including a set of materials distributed in a medium to exhibit a random pattern of partial gamma ray absorption over different positions of the set of materials such that gamma ray emission from a breast traveling through the CSA is partially absorbed and is partially scattered by the random pattern to produce an output gamma ray radiation pattern having gamma rays in a range of different directions, a gamma imaging device configured to collect gamma rays from the output gamma ray radiation pattern produced by the CSA to convert the collected gamma rays of the breast gamma ray emission from the breast into imaging signals representing an image of the breast, and an imaging processing device configured to reconstruct images in 2D or 3D based on a spatial distribution of the collected gamma rays from the breast.

18 Claims, 10 Drawing Sheets

(56) References Cited

U.S. PATENT DOCUMENTS

| | | | | |
|---|---|---|---|---|
| 8,299,437 | B2* | 10/2012 | Nakamura | G01T 1/1603 250/361 R |
| 9,864,072 | B2* | 1/2018 | Li | G01T 1/202 |
| 10,067,245 | B2* | 9/2018 | Li | A61B 6/032 |
| 10,365,385 | B2* | 7/2019 | Li | G01N 23/046 |
| 10,578,753 | B2* | 3/2020 | Li | G01N 23/046 |
| 2010/0301221 | A1* | 12/2010 | Nakamura | G01T 1/1603 250/366 |
| 2017/0192107 | A1* | 7/2017 | Li | A61B 6/032 |
| 2018/0038967 | A1* | 2/2018 | Li | G01T 1/2928 |
| 2018/0321400 | A1* | 11/2018 | Li | G01T 1/2928 |
| 2019/0317228 | A1* | 10/2019 | Li | G01T 1/2006 |
| 2020/0113529 | A1* | 4/2020 | Obrzut | A61B 6/502 |

OTHER PUBLICATIONS

Bache et al., Quantification of tumor uptake with molecular breast imaging. Med Phys. Jun. 10, 2017., pp. 4593-4607.
"Boyd et al., "Mammographic breast density and the risk and detection of breast cancer," N. Engl. J. Med. 356, 227-236 (2007)."
Brem et al., "Occult breast cancer: Scintimammography with high resolution breast-specific gamma camera in women at high risk for breast cancer," Radiology 237, 274-280 (2005).
Candes et al., Stable signal recovery from incomplete and inaccurate measurements. Communications on Pure and Applied Mathematics 59 (8): 1207-1223. Dnoho, D.L. (2006). "Compressed sensing". IEEE Transactions on Information Theory 2006 52 (4): 1289-1306.
Chan et al., Characterization of Breast Masses in Digital Breast Tomosynthesis and Digital Mammograms: An Observer Performance Study. Acad Radiol. Jun. 21, 2017. pii: S1076-6332(17)30220-9.
Covington et al., Molecular Breast Imaging and the 2016 Update to the ACR Appropriateness Criteria for Breast Cancer Screening, J Am Coll Radiol. Dec. 2016;13(12 Pt A):1408.
Depuey et al., "Patient-centered imaging," J. Nucl. Cardiol. 19, 185-215 (2012).
Dickerscheid et al., Contrast-noise-ratio (CNR) analysis and optimisation of breast-specific gamma imaging (BSGI) acquisition protocols. EJNMMI Res. Mar. 25, 2013;3(1):21.
Duarte et al., Single-Pixel Imaging via Compressive Sampling. pp. 83-91. IEEE Signal Processing Magazine, Mar. 2008, vol. 25, Issue: 2.
Gong et al., Comparison of breast specific gamma imaging and molecular breast tomosynthesis in breast cancer detection: Evaluation in phantoms. Med Phys. Jul. 2015;42(7):4250-9.
Grant et al., CVX: Matlab software for disciplined convex programming, version 2.0 beta. http://cvxr.com/cvx, Sep. 2013.
Harvey et al., "Quantitative assessment of mammographic breast density: Relationship with breast cancer risk," Radiology 230, 29-41 (2004).
Hendrick et al., "Radiation doses and cancer risks from breast imaging studies," Radiology 257, 246-253 (2010).
Hruska et al., "Curies, and Grays, and Sieverts, Oh My: A guide for discussing radiation dose and risk of molecular breast imaging," J. Am. Coll. Radiol. 12, 1103-1105 (2015).
Hruska et al., Proof of concept for low-dose molecular breast imaging with a dualhead CZT gamma camera. Part II. Evaluation in patients. Med Phys. Jun. 2012;39(6):3476-83.
Hruska et al., Nuclear imaging of the breast: translating achievements in instrumentation into clinical use. Med Phys. May 2013;40(5):050901.
Kolb et al., Comparison of the performance of screening mammography, physical examination, and breast US and evaluation of factors that influence them: an analysis of 27,825 patient evaluations. Radiology. Oct. 2002;225(1):165-75.
Koral et al., Testing of local gamma-ray scatter fractions determined by spectral fitting. Phys Med Biol. Feb. 1991;36(2):177-90.
Long et al., Performance characteristics of dedicated molecular breast imaging systems at low doses. Med Phys. Jun. 2016;43(6):3062-3070.
Mandelson et al., Breast density as a predictor of mammographic detection: comparison of interval- and screen-detected cancers. J Natl Cancer Inst. Jul. 5, 2000;92(13):1081-7.
More et al., "Limited angle dual modality breast imaging," IEEE Trans. Nucl. Sci. 54, 504-513 (2007).
More et al., "Evaluation of gamma cameras for use in dedicated breast Imaging," IEEE Trans. Nucl. Sci. 53, 2675-2679 (2006).
NEMA, "Performance measurements of gamma cameras," in NEMA NU Jan. 2012 (National Electrical Manufacturer Association, Arlington, VA,2013).
O'Connor et al., Molecular breast imaging. Expert Rev Anticancer Ther. Aug. 2009;9(8):1073-80.
Pisano et al., Diagnostic performance of digital versus film mammography for breast-cancer screening. N Engl J Med. Oct. 27, 2005;353(17):1773-83. Epub Sep. 16, 2005.
Rechtman et al., Breast-specific gamma imaging for the detection of breast cancer in dense versus nondense breasts. AJR Am J Roentgenol. Feb. 2014;202(2):293-8.
Rhodes et al., "Molecular breast imaging at reduced radiation dose for supplemental screening in mammographically dense breasts," AJR, Am. J. Roentgenol. 204, 241-251 (2015).
Rosenberg et al., Effects of age, breast density, ethnicity, and estrogen replacement therapy on screening mammographic sensitivity and cancer stage at diagnosis: review of 183,134 screening mammograms in Albuquerque, New Mexico. Radiology. Nov. 1998;209(2):511-8.
Schellingerhout et al., Coded aperture nuclear scintigraphy: a novel small animal imaging technique. Mol Imaging. Oct. 2002;1(4):344-53.
Seco et al., Review on the characteristics of radiation detectors for dosimetry and imaging. Phys Med Biol. Oct. 21, 2014;59(20):R303-47.
Staelens et al., Monte Carlo simulations of a scintillation camera using GATE: validation and application modelling. Phys Med Biol. Sep. 21, 2003;48(18):3021-42.
Tabar et al., Mammography service screening and mortality in breast cancer patients: 20-year follow-up before and after introduction of screening. Lancet. Apr. 26, 2003;361(9367):1405-10.
Wang et al., Compressed wideband spectrum sensing based on discrete cosine transform. Scientific World Journal. Jan. 8, 2014;2014:464895.
Weinmann et al., Design of optimal collimation for dedicated molecular breast imaging systems. Med Phys. Mar. 2009;36(3):845-56.
Williams et al., "Dualmodality tomosynthesis," Radiology 255(1), 191-198 (2010).
Zhang et al., Breast-specific gamma camera imaging with 99mTc-MIBI has better diagnostic performance than magnetic resonance imaging in breast cancer patients: A meta-analysis. Hell J Nucl Med. Jan.-Apr. 2017;20(1):26-35.
Zhang et al., Low-dose CT reconstruction via L1 dictionary learning regularization using iteratively reweighted least-squares. Biomed Eng Online. Jun. 18, 2016;15(1):66.

* cited by examiner

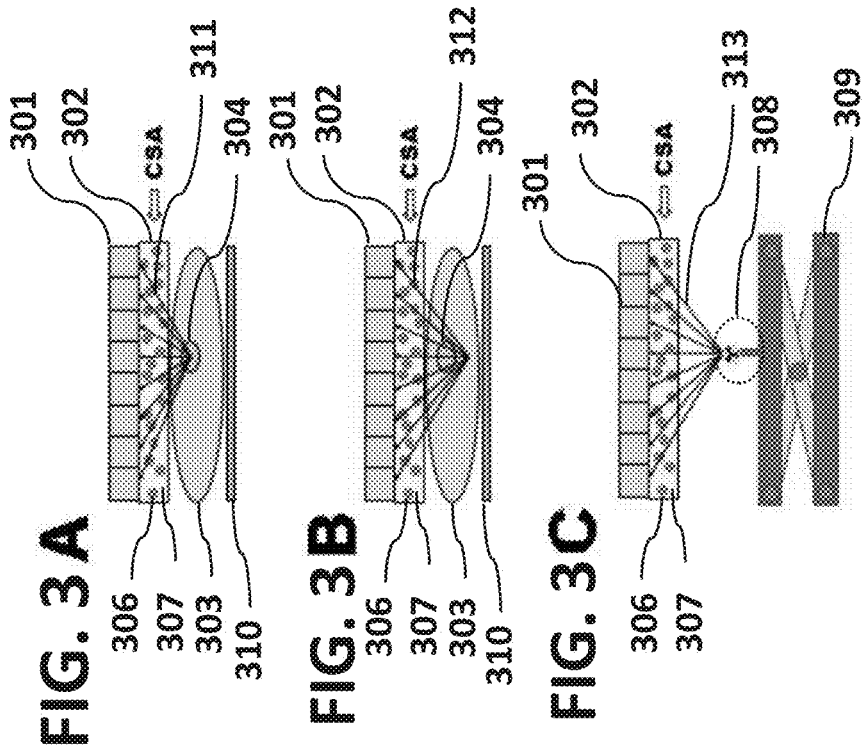

COMPRESSIVE SENSING ABSORBER FOR BREAST IMAGING

PRIORITY CLAIM AND CROSS REFERENCE TO RELATED APPLICATIONS

This patent document claims priority to and benefits of U.S. Provisional Patent Application No. 62/744,566 entitled "COMPRESSIVE SENSING ABSORBER FOR BREAST IMAGING" filed on Oct. 11, 2018. The entire content of the aforementioned patent application is incorporated by reference as part of the disclosure of this patent document.

TECHNICAL FIELD

This patent document relates to image acquisition and reconstruction for breast imaging.

BACKGROUND

Molecular Breast Imaging (MBI) and Breast Specific Gamma Imaging (BSGI) are both specialized nuclear medicine breast imaging techniques that use gamma radiation and require intravenous injection of a radioactive agent to obtain images of the breast by detecting gamma radiation using gamma ray detectors or cameras. The BSGI and MBI have not been widely accepted for breast cancer screening due to greater effective radiation dose compared with mammography, low scanner efficiency, long image acquisition time and lack of 3D imaging capability. Thus, there is a need to develop new techniques to increase scanner efficiency, decrease image acquisition time and allow for ultra-low-dose, high-resolution 2D and 3D molecular breast imaging.

SUMMARY

The technology disclosed in this patent document includes methods, devices and applications pertaining to a compressive sensing absorber (CSA) for molecular breast imaging (MBI) and breast specific gamma imaging (BSGI) that will greatly increase scanner efficiency, decrease image acquisition time and allow for ultra-low-dose, high-resolution 2D and 3D molecular breast imaging.

In an embodiment of the disclosed technology, a breast imaging system includes a compressive sensing absorber (CSA) including a set of materials distributed in a medium to exhibit a random pattern of partial gamma ray absorption over different positions of the set of materials such that gamma ray emission from a breast traveling through the CSA is partially absorbed and is partially scattered by the random pattern to produce an output gamma ray radiation pattern having gamma rays in a range of different directions, a gamma imaging device positioned relative to the CSA to collect gamma rays from the output gamma ray radiation pattern produced by the CSA to convert the collected gamma rays of the breast gamma ray emission from the breast into imaging signals representing an image of the breast, and an imaging processing device coupled to receive image information of the imaging signals from the gamma imaging device and configured to reconstruct images in 2D or 3D based on a spatial distribution of the collected gamma rays from the breast.

In another embodiment of the disclosed technology, an imaging system includes a radioactive source configured to emit gamma ray photons in certain directions toward a sample, a collimator including randomly distributed materials within a medium through which gamma rays from the sample pass at different angles, and a compressive sensing reconstruction hardware configured to perform a compressive sensing reconstruction algorithm to reconstruct the gamma rays from the sample as an image.

In yet another embodiment of the disclosed technology, a compressive sensing absorber (CSA) device includes a set of particles distributed with a predetermined random pattern in a medium such that gamma rays traveling through the medium are partially absorbed and scattered by the set of particles, and a case configured to contain the medium and the set of particles and formed of a material that is transparent to gamma-ray radiation, wherein the case is configured to be attached to a gamma camera used for imaging.

The subject matter described in this patent document can be implemented in specific ways that provide one or more of the following features.

BRIEF DESCRIPTION OF THE DRAWINGS

FIG. 2A shows gamma rays arising from the tumor, and FIG. 2B shows gamma rays arising within breast tissue deep to the tumor.

FIGS. 3A-3C show an example of compressive sensing absorber (CSA) breast specific gamma imaging (BSGI) system including a single gamma detector and CSA placed relative to breast tissue that includes breast tumor nodule. Specifically, FIG. 3A shows gamma rays arising from the tumor, and FIG. 3B shows gamma rays arising within breast tissue deep to the tumor. FIG. 3C shows XYZ plotter that is used to determine the sensing matrix used for image reconstruction by moving a radioactive point source through the desired image voxel grid prior to imaging.

FIG. 6A shows single pinholes, FIG. 6B shows nonoverlapping pinholes, FIG. 6C shows degenerate pinholes, and FIG. 6D shows coded aperture.

FIG. 8A shows a ground truth image, FIG. 8 shows an image generated with 500 Bq×100 or 0.00135 mCi, NMSE=6.74, FIG. 8C shows 500 Bq×500 or 0.00676 mCi, NMSE=0.648, and FIG. 8D shows 500 Bq×1000 or 0.0135 mCi, NMSE=0.2211.

DETAILED DESCRIPTION

Figure 1:
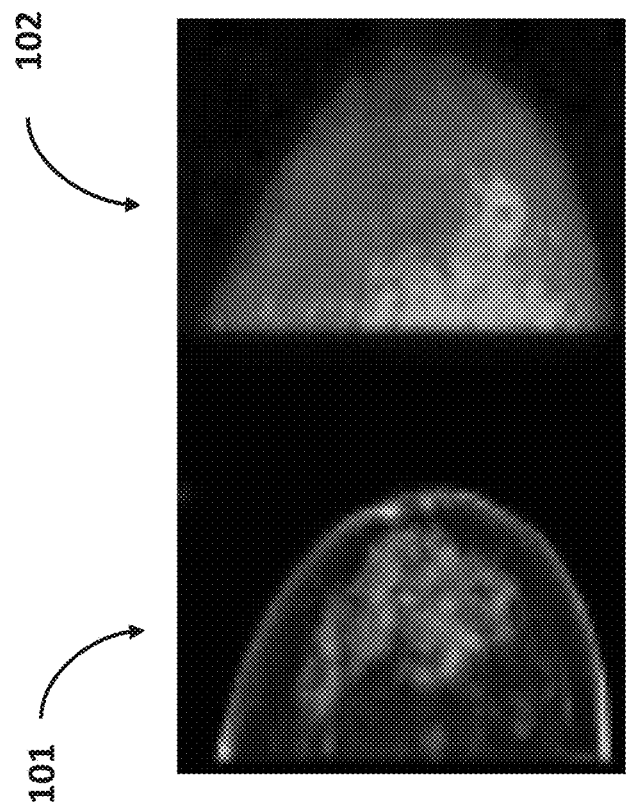
FIG. 1 shows examples of negative mammogram and positive molecular breast imaging (MBI).

The disclosed technology can be implemented to provide various methods, devices and applications pertaining to a compressive sensing absorber (CSA) for molecular breast imaging (MBI) and breast specific gamma imaging (BSGI) that may greatly increase scanner efficiency, decrease image acquisition time and allow for ultra-low-dose, high-resolution 2D and 3D molecular breast imaging. Some embodiments of the disclosed technology include a novel collimator containing a random pattern of attenuation that allows for detection of many more photons, thus greatly increasing sensitivity, and a compressive sensing reconstruction algorithm which, in combination with the hardware, allows for 3D imaging with a stationary camera head that has no moving parts. Some embodiments of the disclosed technology enable image acquisition and reconstruction of a phantom using CSA on MBI gamma camera.

Molecular breast imaging (MBI) and breast specific gamma imaging (BSGI) utilize γ-cameras in a mammographic configuration to provide functional images of the breast. For example, the MBI and BSGI require intravenous injection of a radioactive agent to obtain images of the breast. Several studies have confirmed that MBI has a high sensitivity for the detection of small breast lesions, independent of tumor type. A large clinical trial compared MBI with screening mammography in over 1000 women with mammographically dense breast tissue and increased risk of breast cancer and showed that MBI detected two to three times more cancers than mammography. Despite these favorable results, BSGI and MBI have not been widely accepted for breast cancer screening due to greater effective radiation dose compared with mammography. In addition, the long imaging time of MBI can cause discomfort to the patient. Furthermore, while digital breast tomosynthesis (DBT) produces 3D images, resulting in improved cancer detection over mammography, current clinical MBI and BSGI systems produce only 2D images. Therefore, the use of a parallel hole collimator (PHC) with MBI and BSGI, is inefficient, allowing only gamma rays traveling perpendicular to the detector to be recorded. Furthermore, PHA cannot produce a 3D image with a stationary detector and results in a loss of image resolution with increasing distance between the tumor and the gamma detector.

In some embodiments of the disclosed technology, a compressive coded absorber or a compressive sensing absorber (CSA) may be used as a replacement for the inefficient PHC on the BSGI and MBI systems with a goal of increasing the detection rate of the emitted gamma rays. In some embodiments of the disclosed technology, an injection of a radioactive agent into the patient's body causes gamma rays to arise from breast tissues and tumors, and gamma, and the gamma rays emitted from the breast tissues and tumors travel through the CSA and are partially absorbed and scattered by the predetermined random pattern. In some embodiments of the disclosed technology, the CSA includes a sensing matrix with a predetermined random pattern of partial gamma ray absorption. For example, the sensing matrix of materials may be structured to exhibit a random pattern of partial gamma ray absorption over different positions of the matrix such that breast gamma ray emission from a breast traveling through the CSA is partially absorbed and is partially scattered by the random pattern to produce an output gamma ray radiation pattern having gamma rays in a range of different directions. Gamma rays traveling through the CSA are partially absorbed and scattered by the predetermined random pattern and recorded by a gamma imaging device such as a stationary gamma detector. In some embodiments of the disclosed technology, the gamma imaging device is positioned relative to the CSA to collect gamma rays from the output gamma ray radiation pattern produced by the CSA to convert the collected gamma rays of the breast gamma ray emission from the breast into imaging signals representing an image of the breast. In addition, an imaging processing device may be coupled to receive image information of the imaging signals from the gamma detector array to reconstruct images in 2D or 3D based on a spatial distribution of the collected gamma rays from the breast. For example, images are reconstructed in 2D or 3D using compressed sensing (CS) framework based on underlying sparsity in the breast gamma ray emission. In contrast to the PHA, the CSA architecture allows for a stationary gamma detector to collect gamma-ray measurements at all relevant angles. In some embodiments of the disclosed technology, the design of a CSA gamma camera system may be optimized using a detailed Monte Carlo simulation. Some embodiments of the disclosed technology may be used to replace the current inefficient PHC with CSA for 2D and 3D MBI and BSGI. The CSA gamma camera system implemented based on some embodiments of the disclosed technology may greatly decrease patient imaging time compared with PHC MBI, and allow for ultra-low-dose, high-resolution molecular breast imaging and cancer screening in dense breasts.

As discussed above, the MBI and BSGI can detect cancer in dense breasts but they have not been widely accepted for breast cancer screening due to greater effective radiation dose compared with mammography. The CSA for MBI and BSGI implemented based on some embodiments of the disclosed technology may decrease radiation dose and imaging time of gamma ray imaging, and may allow for high-resolution molecular breast imaging and cancer screening in dense breasts. The CSA for MBI and BSGI implemented based on some embodiments of the disclosed technology may decrease the effective radiation dose even moderately below current levels 1.2-2.4 mSv for MBI and closer to those of a screening mammogram of 0.7-1.0 mSv, and it may be considered for inclusion in the American College of Radiology (ACR) Appropriateness Criteria for Breast Cancer Screening and gain widespread use in the detection of breast cancer, particularly in dense breasts.

The CSA camera system implemented based on some embodiments of the disclosed technology may achieve a high sensitivity and spatial resolution. When comparing the sensitivity of the CSA with a parallel hole collimator (PHC) by performing extrinsic and intrinsic floods using a Digirad Ergo gamma camera, the CSA camera system implemented based on some embodiments of the disclosed technology allows for collection of over six hundred times more gamma rays than the PHA system over the same time period. If the CSA camera system can achieve comparable resolution to PHA system, this would represent a great increase in efficiency, potentially allowing for ultra-low dose molecular breast imaging. While the sensitivity/resolution tradeoff for the CSA gamma camera system needs to be determined, the CSA approach offers several novel characteristics for potentially improving resolution. For example, unlike PHA which demonstrates loss of resolution with increasing distance, the predetermined 3D image grid implemented with the CS reconstruction may result in preserved resolution at increasing distance.

In some embodiments of the disclosed technology, reconstruction algorithms in coded aperture imaging may be used to acquire high resolution images at very low sensitivity, greater than sensitivity of a pinhole collimator. Reconstruction with a coded aperture can be achieved using a relatively small number of symmetrically spaced low-sensitivity pinholes positioned in a lead or tungsten plate. Unlike the reconstruction algorithms in coded aperture imaging, compressive sensing algorithms implemented based on some embodiments of the disclosed technology utilizes a sparsity basis for reconstruction. The CSA relies on a sensing matrix Φ that contains a random pattern with a very large number of known partially absorbing elements, in the order of thousands, allowing for reconstruction of images with many more gamma rays originating from many more locations and angles in the breast tissue.

The CSA based on some embodiments of the disclosed technology offer a significant advantage over existing methodologies in nuclear medicine. The CSA system offers 3D MBI with a stationary detector/CSA positioned relative to the compressed breast and novel 3D reconstruction algorithm which does not use a sinogram. In some implementations, MBI is clinically performed in 2D and attempts at 3D imaging have utilized limited angle approach with a sonogram. The maximum likelihood expectation maximization (MLEM) reconstruction is restricted by the small number of angles, and the PHA system needs to be moved away from the breast, which decreases resolution.

The MBI and BSGI images of each compressed breast are typically acquired in the craniocaudal and mediolateral oblique projections following IV injection of Tc-99m Sestamibi. The MBI may have slightly better specificity than mammography. Studies using MBI have shown that this method has comparable sensitivity to breast MRI. Despite these favorable results, BSGI and MBI have not been widely accepted for breast cancer screening due to greater effective radiation dose compared with mammography. The effective dose for single-detector BSGI is approximately 6.5 mSv and 1.2-2.4 mSv for dual-detector MBI. By comparison, a screening mammogram has an effective dose of 0.7-1.0 mSv. Another disadvantage of MBI is long imaging time (4×10-min images), causing discomfort to the patient. Furthermore, while digital breast tomosynthesis (DBT) produces 3D images, resulting in improved cancer detection over mammography, current clinical MBI and BSGI systems produce only 2D images, due to the use of parallel hole collimator (PHC) with MBI and BSGI, which is inefficient, allowing only gamma rays traveling perpendicular to the detector to be recorded. Furthermore, PHA cannot produce a 3D image with a stationary detector and results in a loss of image resolution with increasing distance between the tumor and the gamma detector using limited angle acquisition.

The CSA implemented based on some embodiments of the disclosed technology may include a sensing matrix with pre-determined random pattern of partial gamma ray absorption. In one example, the sensing matrix may include small steel ball bearings and ballistic gel mixture in an acrylic case. Gamma rays traveling through the CSA are partially absorbed and scattered by the pre-determined random pattern and recorded by a stationary gamma detector. Images are reconstructed in 2D or 3D using the CS framework based on underlying sparsity in the breast emission images in bases such as the discrete cosine transform (DCT). The CSA sensing matrix is first determined only once before all imaging using a radioactive point source, which is sequentially positioned at each voxel of the intended 2D or 3D image grid using an XYZ point source plotter implemented based on some embodiments of the disclosed technology and solving a system of linear equations. In contrast to the PHA, the CSA architecture allows for a stationary gamma detector to collect gamma ray measurements at all relevant angles, rather than only detecting gamma rays traveling perpendicularly to the detector. In some embodiments of the disclosed technology, the design of a CSA gamma camera system may be optimized using a detailed Monte Carlo simulation and to assess prototype performance. Some embodiments of the disclosed technology may be implemented to create a compressive sensing absorber (CSA) for MBI and BSGI that will greatly increase scanner efficiency, decrease image acquisition time and allow for ultra-low-dose, high resolution 2D and 3D molecular breast imaging.

Breast cancer continues to be the most prevalent malignancy in American women. The American Cancer Society estimates that in 2017 there will be 252,710 new cases of invasive breast cancer. Breast cancer screening has evolved from (a) film screen mammography trials in 1960s to the early 1980s to (b) the 2005 Digital Mammographic Imaging Screening Trial (DMIST) trial showing superiority of full-field digital mammography (FFDM) in dense breast to (c) current studies documenting improved detection of breast cancer in dense breasts with the use of the DBT. Based on film screen mammography trials, there has been a 34% decrease in breast cancer mortality since 1990. Despite all the significant progress in mammographic screening, evaluation of patients with dense breasts, both in the screening and diagnostic settings, continues to be a significant challenge that requires evaluation of new technologies as adjuncts to mammography. The dynamic contrast enhanced (DCE) breast MRI has emerged as an important supplemental imaging modality. However, MRI is limited by (i) patient body habitus, (ii) claustrophobia, (iii) certain implantable devices (defibrillators, cochlear implants), (iv) long imaging time and (v) relatively high cost. Even with the advances in mammography and DCE MRI, there is a need for development of additional imaging modalities to screen and evaluate extent of breast cancer.

FIG. 1 shows examples of negative mammogram 101 and positive molecular breast imaging (MBI) 102. The molecular breast imaging (MBI) and breast specific gamma imaging (BSGI) are novel modalities that use a gamma camera in a mammographic configuration to obtain functional images of Tc-99m Sestamibi uptake in the breasts. Tc-99m Sestamibi is thought to localize in breast cancer due to increased mitochondrial activity. The MBI uses two solid state gamma detectors and the BSGI uses a single detector. Both the MBI and BSGI systems can be used for detecting cancers occult on mammography, particularly in dense tissue, as shown in FIG. 1. A study of 341 women with biopsy-proven breast cancer suggests that the sensitivity of BSGI is similar in women with dense (94.7%) and non-dense breasts (96.5%). In general, MBI studies with CZT solid state detectors have reported sensitivities of 82%-91% for breast tumors less than 10 mm in size. The sensitivity of mammography, on the other hand, ranges from 71% to 96% when averaged over all breast types, but decreases to 68% in women with radiographically dense breasts and to 48% in women with extremely dense breasts. Nevertheless, women with radiodense breast tissue have up to six times greater lifetime risk of being diagnosed with breast cancer than do those with non-dense breast.

The MBI and BSGI demonstrate greater effective radiation dose than mammography and require longer imaging time. Despite many advantages, including the ability to detect cancer in dense breasts, the MBI and BSGI have not been accepted for breast cancer screening due to greater effective radiation dose compared with mammography. The BSGI exams have traditionally been performed with an estimated effective dose to the body of 6-9 mSv. By comparison, the average effective dose from digital mammography is 0.5 mSv and 1.2 mSv with digital breast tomosynthesis (DBT). Reducing the administered doses of Tc-99m Sestamibi to 150-300 MBq in recent MBI studies resulted in effective doses of 1.2-2.4 mSv to the body by using two optimized solid-state detectors. Furthermore, MBI and BSGI require long imaging time. To perform MBI, the patient's breast is compressed between the detectors. For the BSGI, a single detector and a paddle are used. This process is performed four (or more) times, with craniocaudal (CC) and mediolateral oblique (MLO) projection views obtained of each breast. A typical acquisition time of 10 minutes/view, with total imaging time of 40 minutes, is not comfortable for the patient.

Current clinical MBI/BSGI is two-dimensional, which can limit potential performance. The DBT, a limited angle 3D version of the mammogram demonstrates better performance than mammography. Similarly, it would be expected that the molecular breast tomosynthesis (MBT), a 3D version of MBI, would be superior to 2D MBI as well. Limited-angle MBT, when added to the DBT, has demonstrated improvements in specificity and positive predictive value compared to the DBT. The limited-angle MBT has been difficult to implement in clinical practice because the detectors need to be moved to acquire images at various angles.

In some embodiments of the disclosed technology, a compressive sensing absorber (CSA) may be added to the MBI/BSGI system to (1) greatly decrease effective radiation dose, (2) shorten imaging time and (3) enable a novel 3D image reconstruction with stationary detectors.

Figure 2A:
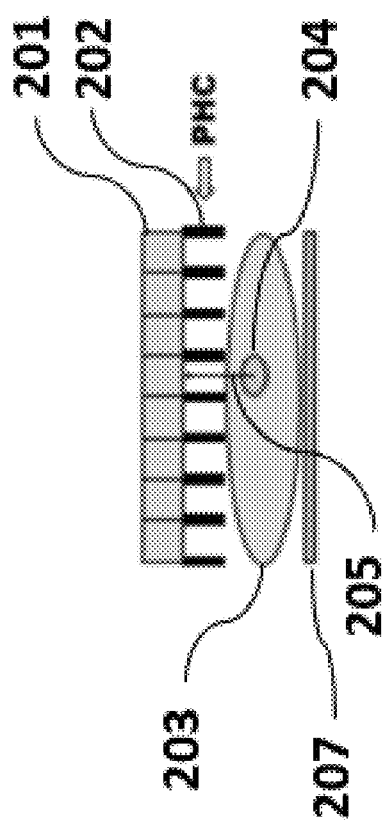
FIGS. 2A and 2B show parallel hole collimator (PHC) breast specific gamma imaging (BSGI) system with a single gamma detector and lead PHC placed adjacent to breast tissue including breast tumor nodule. Specifically.
Figure 2B:
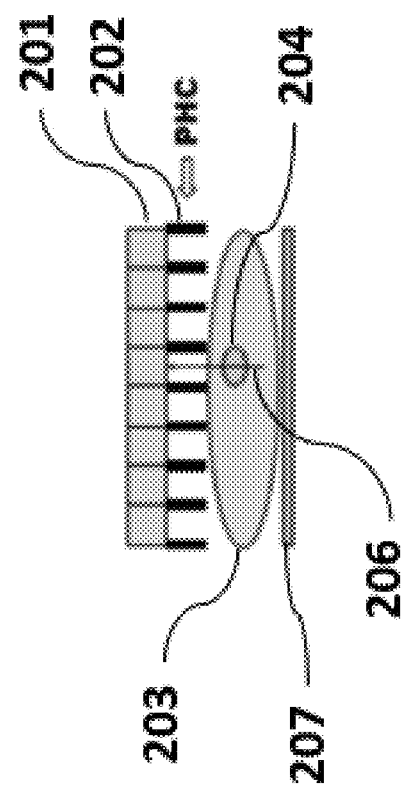

FIG. 2, which includes FIGS. 2A and 2B, shows an example device structured as a parallel hole collimator (PHC) breast specific gamma imaging (BSGI) system with a single gamma detector 201 and lead PHC 202 placed adjacent to breast tissue 203 including breast tumor nodule 204. Specifically, FIG. 2A shows gamma rays 205 emitted from the radiative agent injected into the tumor nodule 204 where the breast tissue 203 is placed between the PHC and a plate 207, and FIG. 2B shows gamma rays 206 emitted by the injected radioactive agent within breast tissue deep to the tumor nodule 204 where the breast tissue 203 is placed between the PHC and the plate 207. In the illustrated example, only gamma rays which are primarily traveling perpendicular to the detector are recorded.

The collimator on the MBI/BSGI systems can be replaced with a compressive sensing absorber (CSA) to increase sensitivity based on some embodiments of the disclosed technology. In the context of this patent document, a compressive sensing absorber (CSA) can indicate a structure that includes a set of materials distributed in a medium to exhibit a random pattern of partial gamma ray absorption over different positions of the set of materials such that gamma ray emission from a breast traveling through the CSA is partially absorbed and is partially scattered by the random pattern to produce an output gamma ray radiation pattern having gamma rays in a range of different directions. Unlike the MBI and BSGI, which use an inefficient lead parallel hole collimator (PHC) to localize the origin of the gamma rays being emitted from breast tissue, the imaging system implemented based on some embodiments of the disclosed technology uses the CSA allowing for reconstruction of images with many more gamma rays originating from many more locations in the breast tissue. Unlike the PHC, which allows primarily for gamma rays 205 perpendicular to the detector to reach the detector, the imaging system implemented based on some embodiments of the disclosed technology uses the CSA allowing for reconstruction of images with many more gamma rays originating from many more angles in the breast tissue. Unlike the imaging system using the PHC, which can detect a very small percentage of emitted photons, resulting in long acquisition time, high radiation dose and Poisson noise, the imaging system including the CSA implemented based on some embodiments of the disclosed technology can detect many more photons and thus can reduce the acquisition time.

FIG. 3, which includes FIGS. 3A-3C, shows an example of compressive sensing absorber breast specific gamma imaging (CSA BSGI) system including a single gamma detector 301 and a compressive sensing absorber (CSA) 302 placed relative to a breast tissue 303 that includes breast tumor nodule 304. Specifically, FIG. 3A shows gamma rays 311 arising from the tumor nodule 304 where the breast tissue 303 is placed between the CSA 302 and a plate 310, and FIG. 3B shows gamma rays 312 arising within breast tissue deep to the tumor nodule 304 where the breast tissue 303 is placed between the CSA 302 and the plate 310. In some implementations, the gamma imaging system with the CSA may include a radiation source 308 and a XYZ plotter 309 to move the radioactive light source 308 in X, Y, and Z directions. In some implementations, the radioactive light source 308 may be a radioactive point source. FIG. 3C shows a XYZ plotter 309 that is used to determine the sensing matrix used for image reconstruction by using an xyz positioning device to change the three-dimensional position of the radiation source 308 with respect to the breast tumor nodule 304.

In some embodiments of the disclosed technology, the CSA may include ballistic gel 307 with steel ball bearings 306. The detector 301 can detect gamma rays 311, 312, 313 at all relevant angles, unlike the PHC collimator. The XYZ plotter is used to determine the sensing matrix used for image reconstruction by moving the radioactive point source 308 through the desired image voxel grid prior to imaging. A radioactive point source is a single identifiable localized source of radioactive radiation. Gamma ray and X-ray sources may be treated as point sources, which can be approximated as a mathematical point to simplify analysis, if they are sufficiently small.

In order to reduce the injected radiotracer dose and imaging time, it is necessary to greatly increase the sensitivity of the MBI/BSGI system and to collect many more gamma rays emitted from breast tissue. For that end, a gamma camera system implemented based on some embodiments of the disclosed technology includes a compressive sensing absorber (CSA) 302, which includes randomly distributed steel ball bearings 306 within a matrix of ballistic gel 307 as illustrated in FIGS. 3A-3C. Gamma rays 311, 312, 313 emitted from the breast tissue 303, 304 travel through the CSA 302 to reach the gamma detector 301. Some of the gamma rays 311, 312, 313 undergo partial absorption and scatter due to the presence of the steel bearings 306. The sensitivity of the gamma camera system including CSA may be greatly increased because it allows for the gamma detector 301 to collect gamma rays 311, 312, 313 from all relevant angles, rather than only gamma rays traveling perpendicular detector, as in the case of the PHC. Furthermore, by accurately modeling the scattering process, both absorbed and scattered gamma rays 311, 312, 313 by the CSA may be used for image reconstruction to further increase sensitivity.

Figure 4:
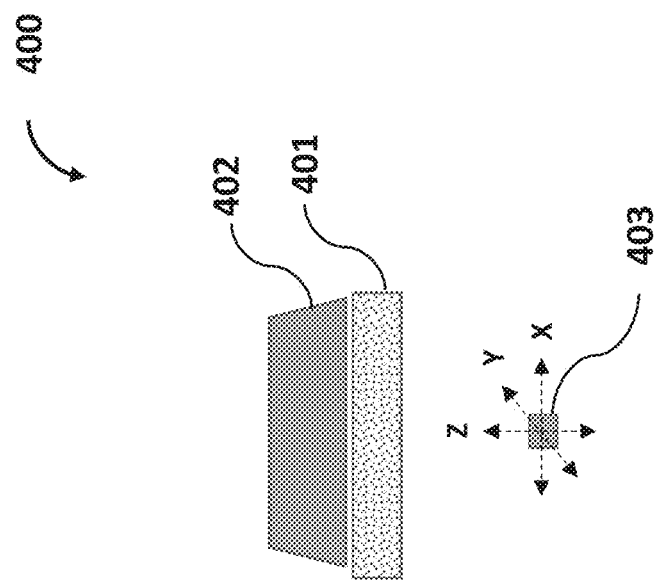
FIG. 4 shows an example of compressive sensing absorber (CSA) radiation imaging system implemented based on some embodiments of the disclosed technology.

FIG. 4 shows an example of compressive sensing absorber (CSA) radiation imaging system 400 implemented based on some embodiments of the disclosed technology.

In some embodiments of the disclosed technology, the CSA radiation imaging system 400 may include a compressive sensing absorber (CSA) device 401, a radiation detector 402, and a radioactive point source 403. In some implementations, the CSA device 401 may include a CSA medium (e.g., ballistic gel) and a set of materials such as particles (e.g., steel ball bearings) randomly distributed in the CSA medium. In one example, the CSA device 401 may further include an acrylic case that contains the ballistic gel and steel ball bearings, and one or more handles for attachment to the gamma detector 402. In some implementations, the CSA device 401 may include the ballistic gel and the steel bearings as construction material since these can be easily removed from the acrylic case and new material can be inserted with a different pattern of gamma ray absorption for prototyping and optimization of the sensing matrix.

In some implementations, the radioactive point source 403 may be structured to move through a predetermined image grid in front of the CSA device 401 and the gamma detector 402. In one example, the CSA radiation imaging system 400 may further include a 3D plotter such as an XYZ point source plotter capable of moving the radioactive point source 403 within a 3D grid, representing voxels of the image to be obtained. In some implementations, the XYZ point source plotter may be constructed with the capability of moving radioactive point source in a cube within 0.1 mm accuracy. In one example, the CSA may include various patterns of the desired image grid, for example 16×16×1 or 100×50×3 with 3×3×3 mm or 6×6×6 mm voxel size.

In some embodiments of the disclosed technology, the CSA includes a case filled with a randomly arranged mixture of steel ball bearings (e.g., 3 mm diameter) in ballistic gel. The CSA may be attached to a gamma camera as a replacement for PHC. Sensing matrix (Phi) may be obtained by acquiring a certain number (e.g., 256) of dynamic images (e.g., 6.5 mm voxel size) of a radioactive point source (e.g., 1-125, 37 MBq) moving through all voxel locations (e.g., 5 sec. per image) at 6 cm away from the gamma detector. Next, separate images of a point source and a phantom (three-point sources) may be acquired and reconstructed using compressive sensing framework. In an embodiment of the disclosed technology, reconstruction may be performed by minimizing total variation (TV), subject to norm (Phi*x-y,2). In another embodiment of the disclosed technology, reconstruction can be performed using machine learning. Normalized mean squared error (NMSE) may be calculated to evaluate the quality of the reconstructions. In one example, a model of the CSA, low energy general purpose PHC and gamma detector may be constructed in image acquisition simulations (e.g., GATE/Geant4 and Monte Carlo) of a point source (e.g., 1-125 point source) (5, 10, 15, 20 cm from detector) and phantom may be performed, followed by image reconstruction. Full width at half maximum (FWHM) and sensitivity may be compared for CSA and PHC in the simulation for radioactive point source and NMSE may be calculated for reconstructed phantom images.

Phantom images (16×16) acquired with the gamma camera may be reconstructed with compressing sensing framework using measurement matrices (MM) that may be overdetermined (e.g., MM 64×64, NMSE=0.5037; MM 32×32, NMSE=0.3398), completely determined (e.g., MM 16×16, NMSE=0.4125) and underdetermined (e.g., MM 12×12, NMSE=0.3776). Monte Carlo simulation demonstrated FWHM for CSA as follows: 7.49 mm at 5 cm, 8.26 mm at 10 cm, 8.89 mm at 15 cm, and 9.26 mm at 20 cm and sensitivity is 309,893 CPM/uCi. The FWHM for PHA is 9.47 mm at 5 cm, 10.22 mm at 10 cm, 10.57 mm at 15 cm, 11.47 mm at 20 cm and sensitivity is 1,084 CPM/uCi. Phantom images (16×16) from Monte Carlo simulation may be then reconstructed using measurement matrices (MM) that are overdetermined (e.g., MM 64×64, NMSE=0.4357; MM 32×32, NMSE=0.3821), completely determined (e.g., MM 16×16, NMSE=0.2505) and underdetermined (e.g., MM 12×12, NMSE=0.4095)

Figure 5:
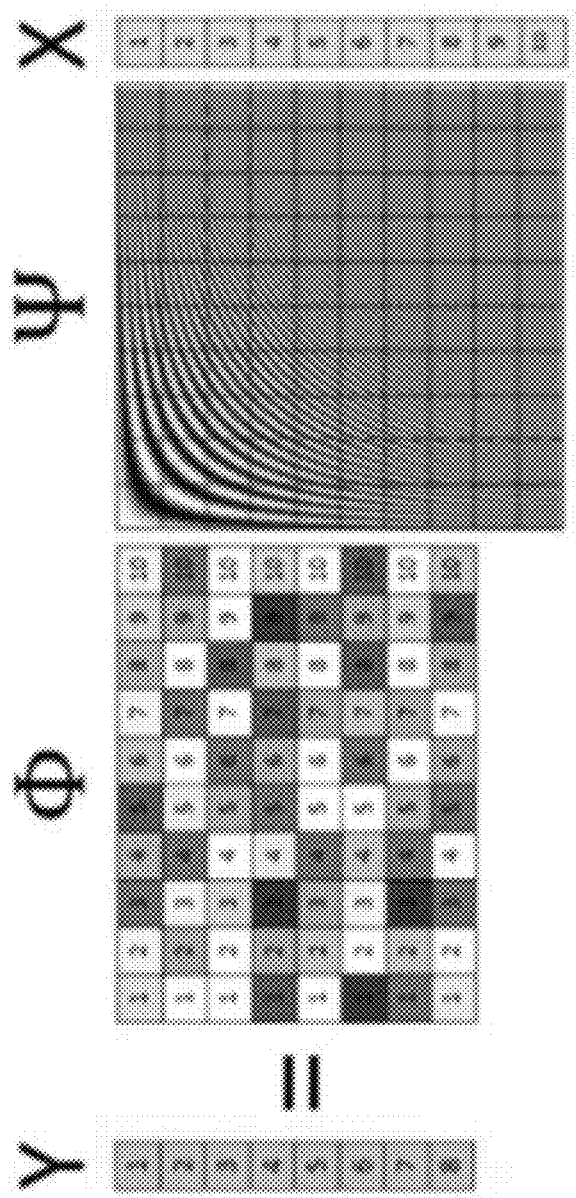
FIG. 5 shows the compressive sensing (CS) framework used to reconstruct images of the breast.

FIG. 5 shows an example of the compressive sensing (CS) framework used to reconstruct images of the breast. Here, "Y" represents CS measurements collected by the gamma detector, "D" is the sensing matrix with a random pattern, represented by ballistic gel with randomly distributed steel ball bearings, and "Ψ" is the discrete cosine transform (DCT), and "X" represents sparse components of the DCT used to reconstruct the emission image X'. Image reconstruction may be performed using L1 minimization of X as shown in FIG. 5.

In some embodiments of the disclosed technology, reconstructing image with the CS framework to allow 2D and 3D imaging with a stationary gamma detector may be conducted in the following way. Image reconstruction using gamma rays passing through the CSA at many different angles and originating at various depths in tissue can be accomplished due to the fact that natural images are sparse in specific bases, for example, the discrete cosine transform (DCT). A 2D or 3D image X' of the breast can be represented as a vector in terms of sparse components X of the DCT, with DCT designated as matrix Ψ in Equation 1 below. Through the CS framework, image reconstruction can be performed, for example, using L1 minimization (FIG. 5) which enforces sparsity. Furthermore, CS theory states that less CS measurements in Y are needed than pixels in image X' for reconstruction of a perfect image with very high probability. The CS reconstruction problem can be stated as:

$$\min\|X\|_{L1} \text{ subject to } Y=\Phi\Psi X \quad (\text{Eq. 1})$$

The quality of the CS reconstruction is dependent on sensing matrix $\Phi$. In the example of the CSA gamma camera system implemented based on some embodiments of the disclosed technology, the sensing matrix is represented by the random pattern of ball bearings within ballistic gel. If components of the sensing matrix are random, then independent measurements Y can be collected for high quality reconstruction. The size and the distribution of steel ball bearings will determine image resolution, sensitivity, scatter and the probability of collecting independent measurements.

In some embodiments of the disclosed technology, an XYZ point source plotter is used to determine the sensing matrix $\Phi$ for the CSA only once prior to all imaging. Since the CSA is composed of randomly distributed steel ball bearings, the sensing matrix $\Phi$ is unknown. In order to determine the sensing matrix, the XYZ radioactive point source plotter may be used. Prior to imaging with the CSA gamma camera system, a radioactive point source with a physical size of a single voxel (e.g., 3×3×3 mm) of the intended image to be reconstructed is mounted on the XYZ plotter, as illustrated in FIG. 3C. Subsequently, the grid of image to be reconstructed is chosen, for example 128×128×1 (3 mm×3 mm×6 cm voxels) for 2D imaging, or 128×128×20 (3 mm×3 mm×3 mm voxels) for 3D imaging. The XYZ plotter moves the radioactive point source through the predetermined image grid in front of CSA and the detector. CS measurements Y are collected. Since a radioactive point source is used, all components of vector X' are zero except for the location of the radioactive point source. This allows for solving for all columns of the sensing matrix $\Phi$. Through this process, non-scattered and scattered gamma rays can be collected and modeled in $\Phi$.

The improvement in sensitivity may be measured by comparing the sensitivity of the CSA with PHC by performing extrinsic flood measurements. The CSA camera system allows for collection of over six hundred times more gamma rays than the PHA system over the same time period. If the CSA camera system can achieve comparable resolution to PHA system, this would represent a great increase in efficiency, potentially allowing for ultra-low dose molecular breast imaging. While the sensitivity/resolution tradeoff for the CSA gamma camera system needs to be determined, the CSA approach offers several novel characteristics for potentially improving resolution. For example, unlike the PHA, which demonstrates loss of resolution with increasing distance, the predetermined 3D image grid implemented with the CS reconstruction may result in preserved resolution at increasing distance away from the detector.

Figure 6:
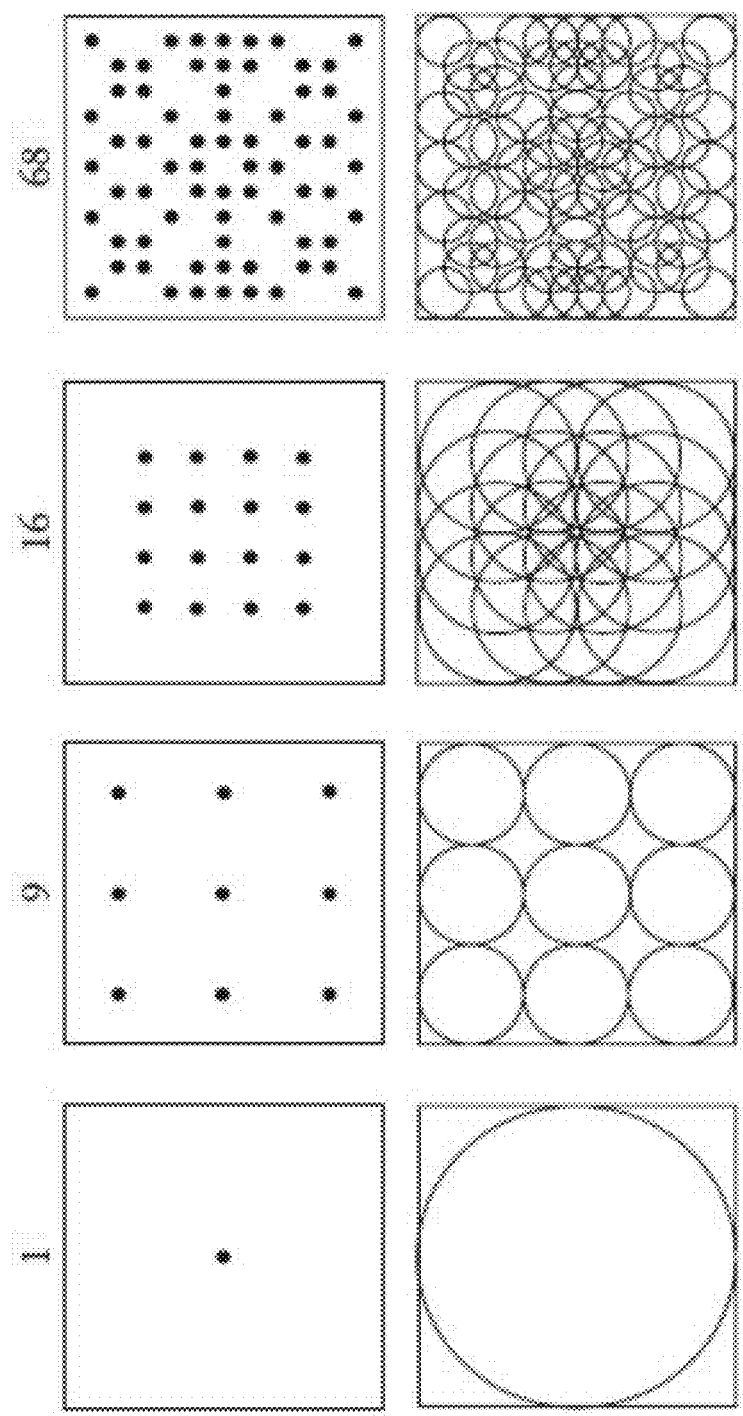
FIGS. 6A-6D show pinhole geometries. Specifically.

FIGS. 6A-6D show pinhole geometries. Specifically, FIG. 6A shows single pinholes, FIG. 6B shows nonoverlapping pinholes, FIG. 6C shows degenerate pinholes, and FIG. 6D shows coded aperture.

Although there might appear to be similarities, at first glance, between the CSA gamma camera system and gamma imaging with a coded aperture, reconstruction algorithms in coded aperture imaging are intended to acquire high resolution images at very low sensitivity, slightly greater than the sensitivity of a pinhole collimator. 2D reconstruction with a coded aperture can be achieved using a relatively small number, for example 68 in FIGS. 6A-6D, of symmetrically spaced low-sensitivity pinholes within a lead or tungsten plate. The CSA, on the other hand, relies on a sensing matrix Φ that contains a random pattern with a very large number of known partially absorbing elements, for example approximately 60,000 known elements for a 16×16 (256 unknowns) image and 200,000,000 known elements for a 128×128 image (16,384 unknowns). These are coefficients in a linear system of equations in CS framework. The physical elements of Φ do not need to be made of tungsten or lead but only need to partially absorb some of the gamma rays emitted.

In addition, the CS algorithm is quite different than coded aperture imaging since it utilizes a sparsity basis for reconstruction as a prior, which allows for solving a system of equations with a much greater number of unknowns. This allows for image reconstruction at very high sensitivities, much greater than PHA sensitivity. Furthermore, the addition of a sparsity basis to the reconstruction promotes denoising of the image. Finally, to properly focus gamma rays with a coded aperture or pinhole collimator, the imaging system is topically quite large and heavy. The CSA, combined with solid state detectors, on the other hand, is very compact and light, which is an advantage in breast imaging.

In some embodiments of the disclosed technology, the CSA uses a novel 3D reconstruction algorithm that utilizes a stationary detector and does not require a sinogram or limited angle acquisition. Both 2D or 3D reconstructions can be performed with the same algorithm (Eq 1) and just require changing the sensing matrix Φ to accommodate a 2D or 3D image grid. In contrast, a 3D molecular breast tomosynthesis (MBT) systems involve moving the gamma detector and the PHA away from the breast tissue in order to acquire images at limited angles, resulting in loss of resolution through the PHA. Furthermore, moving the MBT detector through limited angles is cumbersome. Finally, limited angle reconstructed 3D images are generally inferior to 180-degree acquisition due to an underdetermined system.

Figure 7:
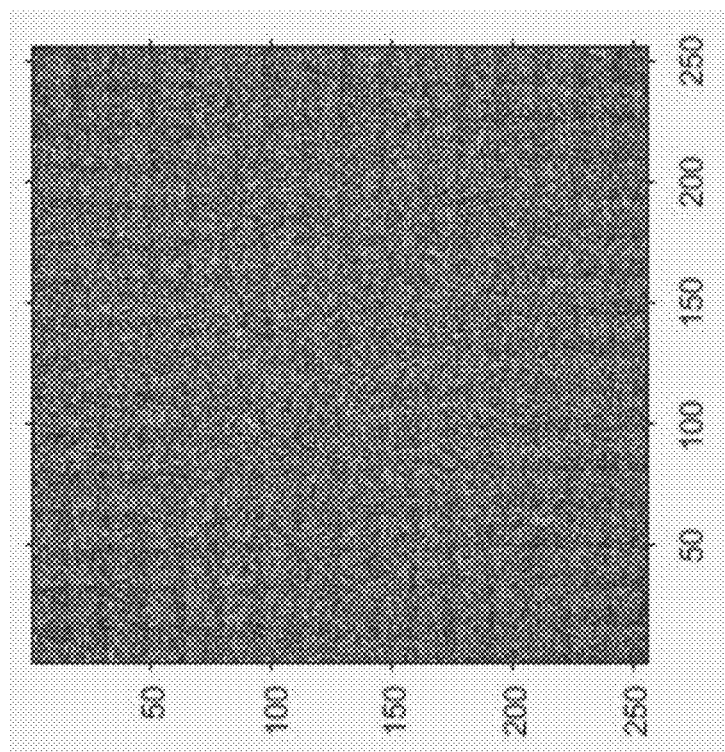
FIG. 7 shows a 256×256 sensing matrix Φ obtained from CS measurements of a radioactive point source moving in a 16×16 grid.

FIG. 7 shows a 256×256 sensing matrix Φ obtained from CS measurements of a radioactive point source moving in a 16×16 grid. The sensing matrix was not completely random on first attempt to construct the CSA with vGATE.

In some implementations, a Monte Carlo simulation of CSA gamma camera system may be performed to demonstrate the feasibility of CSA MBI image acquisition and reconstruction using CS framework. A model of the CSA may be constructed using a random arrangement (e.g., generated with Matlab) of 4 mm steel spheres in an acrylic matrix. For example, a 500 Bq Tc99m source (6×6×6 mm) may be moved in a 16×16×1 image grid (6 mm step) at 20 cm away from CSA gamma camera system. 256 images (CS measurements) may be sequentially acquired with 64×64 matrix (6 mm pixel size). These images may be cropped to obtain CS measurements Y, and 256×256 sensing matrix Φ may be constructed (FIG. 7) as discussed above with reference to FIG. 3C.

Figure 8D:
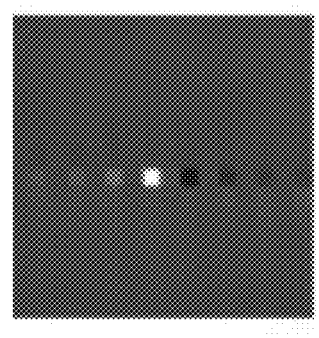
FIGS. 8A-8D show reconstructed 16×16×1 images with 6×6×6 mm pixel size. Specifically.
Figure 8C:
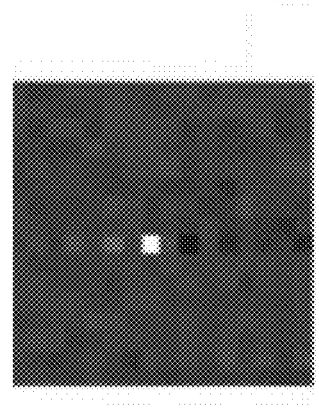
Figure 8B:
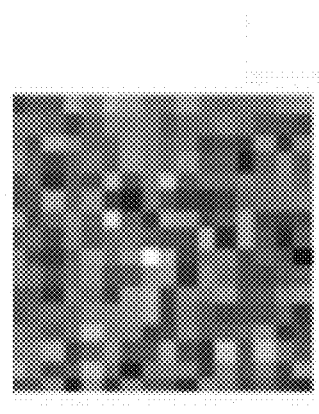
Figure 8A:
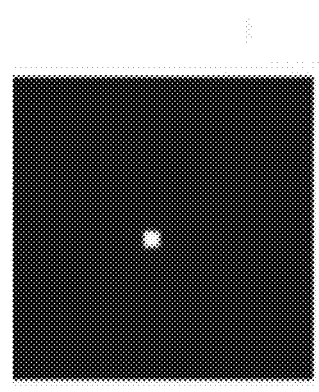

FIGS. 8A-8D show reconstructed 16×16×1 images with 6×6×6 mm pixel size from vGATE 7.2 simulation using L1 minimization and 180 second acquisition time with the radioactive point source 20 cm away from the detector. Specifically, FIG. 8A shows a ground truth image, FIG. 8B shows an image generated with 500 Bq×100 or 0.00135 mCi, NMSE=6.74, FIG. 8C shows 500 Bq×500 or 0.00676 mCi, NMSE=0.648, and FIG. 8D shows 500 Bq×1000 or 0.0135 mCi, NMSE=0.2211. Vertical spot artifact in the center of the images can be attributed to the unintended semi-random pattern in the sensing matrix.

Next, a single image (CS measurements) may be acquired using the 500 Bq radioactive point source in the center of 16×16×1 grid in the eighth row and eighth column. A software (e.g. Matlab) may be used to reconstruct images of the radioactive point source using L1 minimization according to Equation (1). This process may be repeated with 500 Bq radiotracer dose being increased by a factor from 100 to 1000. Normalized mean squared error (NMSE) may be calculated comparing the reconstructed image with ground truth image, as shown in FIG. 8A.

Figure 9:
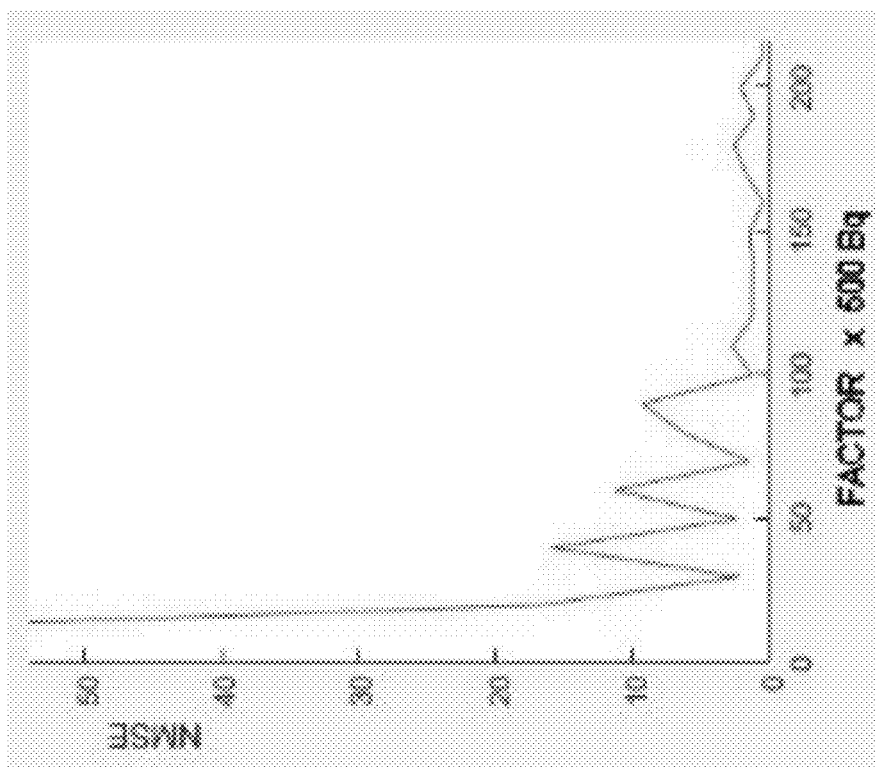
FIG. 9 shows NMSE (vertical axis) decreases with increasing factor (horizontal axis) by which the 500 Bq dose of the radioactive point source is multiplied due to decreasing Poisson noise in the CS measurements.

FIG. 9 shows normalized mean square error (NMSE) (vertical axis) decreases with increasing factor (horizontal axis) by which the 500 Bq dose of the radioactive point source is multiplied due to decreasing Poisson noise in the CS measurements.

The plot in FIG. 9 shows decreasing NMSE of the reconstruction quality with increasing radiotracer dose. A vertical spot artifact is noted on images reconstructed with greater radiotracer doses, which can be attributed to the not completely random pattern in the sensing matrix, as seen in FIG. 7. A high-resolution image was obtained with 0.0135 mCi of Tc99m despite the large distance of 20 cm from the detector.

To perform a preliminary analysis of the sensitivity of the CSA compared to the PAC, intrinsic and extrinsic flood images may be obtained using Cobalt-57 rectangular flood source and a gamma camera. Count rates are measured to demonstrate that the CSA gamma camera system can detect 620 times more gamma rays than PHC system (Table 1 below). To demonstrate the functionality of the XYZ point source plotter and the CSA gamma camera system prototype, 64×64 images (CS measurements) of a 2 mCi I125 point source (brachytherapy seed 0.8 mm×4.6 mm) being moved in a 16×16×1 grid with 6 mm step is acquired.

For example, count rates with Cobalt-57 rectangular flood source are shown in Table 1.

TABLE 1

| Imaging system Count rate (counts/s) | Imaging system Count rate (counts/s) |
|---|---|
| Digirad Ergo Intrinsic Flood 22 × 106 | Digirad Ergo Intrinsic Flood 22 × 106 |
| PHC + Digirad Ergo Extrinsic flood 14 × 103 | PHC + Digirad Ergo Extrinsic flood 14 × 103 |
| CSA + Digirad Ergo Extrinsic flood 8.7 × 106 | CSA + Digirad Ergo Extrinsic flood 8.7 × 106 |

The imaging performance of 2D/3D CSA gamma camera system may be compared with PHC system. The vGATE 7.2 Monte Carlo simulations may be performed to acquire 2D and 3D images of phantoms previously validated in MBI and BSGI. A CS framework will be used to reconstruct images. Subsequently images (Tc99m, I125) are acquired using the camera system implemented based on some embodiments of the disclosed technology and standard gamma camera. The uniformity, sensitivity, energy and spatial resolution, scatter fraction and lesion detection of CSA and PHC systems may be compared. Table 2 demonstrates reconstruction parameters for initial testing. For proof of concept, 3D reconstruction may use 100×50×3 image matrix with 33.1×8.1×6 cm image size.

TABLE 2

| Imaging System | Acquisition Matrix | Available CS Measurements | Used CS Measurements | Reconstructed or Used Matrix | Image Size (cm) | Unknown Elements | Voxel Size (mm) |
|---|---|---|---|---|---|---|---|
| 2D PHC | 128 × 128 | NA | NA | 100 × 50 | 33.1 × 8.1 | NA | 3.31 × 3.24 |
| 2D CSA | 128 × 128 | 16,384 | 5,000 | 100 × 50 × 1 | 33.1 × 8.1 × 6 | 5,000 | 3.31 × 3.24 |
| 2D CSA | 128 × 128 | 16,384 | 4,275 | 100 × 50 × 1 | 33.1 × 8.1 × 6 | 5,000 | 3.31 × 3.24 |
| 2D CSA | 128 × 128 | 16,384 | 3,600 | 100 × 50 × 1 | 33.1 × 8.1 × 6 | 5,000 | 3.31 × 3.24 |
| 3D CSA | 256 × 256 | 65,536 | 15,000 | 100 × 50 × 3 | 33.1 × 8.1 × 6 | 15,000 | 3.31 × 3.24 × 20.0 |
| 3D CSA | 256 × 256 | 65,536 | 12,825 | 100 × 50 × 3 | 33.1 × 8.1 × 6 | 15,000 | 3.31 × 3.24 × 20.0 |
| 3D CSA | 256 × 256 | 65,536 | 10,800 | 100 × 50 × 3 | 33.1 × 8.1 × 6 | 15,000 | 3.31 × 3.24 × 20.0 |

The performance of various CSA absorption fractions for 2D and 3D image reconstruction may be compared. The CS analysis may be optimized by testing various absorption fractions (steel ball bearing density and size in ballistic gel matrix) of the CSA sensing matrix based on intrinsic and extrinsic flood count ratios to find optimal parameters for resolution, sensitivity and lesion contrast. These tests will include both Monte Carlo simulations to acquire 2D and 3D images of validated MBI phantoms and subsequent tests with images acquired with our CSA physical prototype. Scanner geometries are as follows: (a) CSA consisting of randomly arranged steel ball bearings within acrylic case and (b) hexagonal PHC with septal thickness 0.2 mm, hole diameter, 1.5 mm, hole length 23 mm.

source containing water and Tc-99m Sodium Pertechnetate. Both integral and differential uniformity (percentage) may be calculated using standard NEMA techniques. Next, system count sensitivity, as well as PHC and CSA count sensitivity, may be measured. System sensitivity may be measured using a petri dish filled with 7.4 MBq Tc-99m. The dish may be placed directly on the PHC surface and on the CSA surface and imaged for a preset amount of time (300 seconds). The number of counts in the image after background subtraction may be obtained. The system sensitivity in kcts/min/MBq may be obtained by dividing the total number of background subtracted counts by the product of the source activity and the acquisition time. Measurements may be performed using the (1) standard ±10% energy window (126-154 keV), (2) using a wide energy window setting (110-154 keV) that is employed clinically and (3) without an energy window (0-200 keV), since is it not known if selecting an energy window is required for CSA due to modeling of scatter in the sensing matrix for the CSA gamma camera system.

Energy resolution may be assessed intrinsically using a small 4 MBq point source of Tc-99m for 140 keV gamma rays. The detector may be flooded by a Tc-99m point source until a well-defined, smooth photopeak is obtained. Qualitative assessment of extrinsic spatial resolution may be assessed using a 4-quadrant bar-phantom with 2, 2.5, 3, and 3.5 mm bar spacing, at 1-6 cm away from PCH and CSA and using the Tc-99m refillable sheet source. Quantitative assessment of extrinsic spatial resolution may be obtained using a capillary line source (inner diameter 0.7 mm) filled with 20 MBq Tc-99m and imaged at distances of 1-6 cm from the PCH and CSA. Profiles may be shifted in order to align their peaks and generate an averaged line spread function. The full width at half-maximum (FWHM) may be calculated from the averaged line spread function.

For GATE/Geant4 simulation, scatter fraction (SF) may be calculated using the following equation: $SF = (R_{scatter})/(R_{scatter} + R_{true})$ where $R_{true}$ is the number of true events and $R_{scatter}$ is the number of scatter events. For experimental data, the SF may be determined using spectral fitting method. To simulate the hot-spots on the MBI images in clinical practice, a contrast-detail (CD) phantom which shows 'hot' areas or lesions of varying sizes and contrasts in

TABLE 3

| Imaging System | Acquisition Matrix | Available CS Measurements | Grid Shape | Image Size (cm) | Isotope | mCi | Step (sec) | T (hr) | Grid Step (mm) |
|---|---|---|---|---|---|---|---|---|---|
| 2D CSA | 128 × 128 | 16,384 | 100 × 50 × 1 | 33.1 × 8.1 | I 125 | 2 | 43.2 | 60 | 3.31 × 3.24 |
| 2D CSA | 128 × 128 | 16,384 | 100 × 50 × 1 | 33.1 × 8.1 | Tc 99m | 200 | 17.28 | 24 | 3.31 × 3.24 × 20.0 |
| 3D CSA | 256 × 256 | 65,536 | 100 × 50 × 3 | 33.1 × 8.1 × 6 | I 125 | 2 | 14.4 | 60 | 3.31 × 3.24 × 20.0 |
| 3D CSA | 256 × 256 | 65,536 | 100 × 50 × 3 | 33.1 × 8.1 × 6 | Tc 99m | 200 | 5.76 | 24 | 3.31 × 3.24 × 20.0 |

Figure 10:
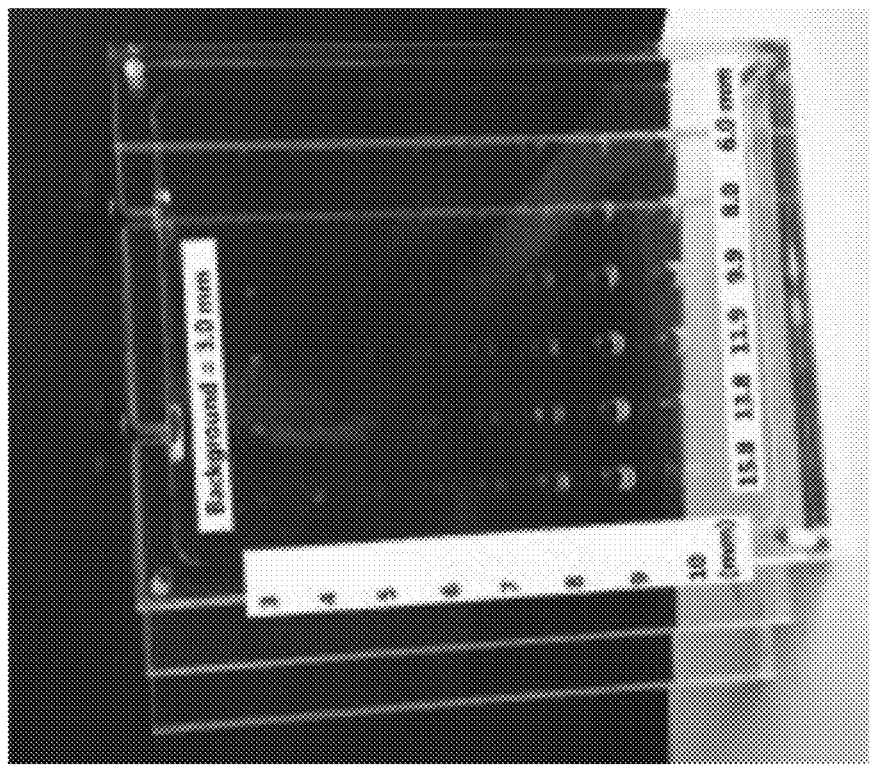
FIG. 10 shows a contrast-detail (CD) phantom used to evaluate MBI camera performance.

FIG. 10 shows a contrast-detail (CD) phantom used to evaluate MBI camera performance. The NEMA standards for assessing the performance characteristics of gamma cameras may be established with conventional gamma cameras. Uniformity may be measured using a refillable sheet known locations in a background that has no cold spots may be constructed as shown in FIG. 10. The phantom may represent lesion/background ratios of 2.0:1, 2.7:1, 3.3:1, 4.0:1, 4.6:1, and 5.3:1 as shown in FIG. 10. The overall 6-cm thickness may be designed to match the typical thickness of the compressed breast observed in clinical MBI studies.

The lesion CNR will be assessed for holes at average depths of 1.5, 3.0, and 4.5 cm from the PHC and CSA face. The CNR may be measured from regions of interest (ROIs) placed over the lesions and adjacent background, using the following equation: CNR=(Max. Lesion Count-Avg. Bkg. Count)/Std. Dev. Bkg. Count. The maximum lesion count may be used instead of average lesion counts as some of the hole diameters may be equivalent or smaller than the pixel size. Lesion CNRs may be compared between the two systems using a nonparametric Wilcoxon Signed Ranks test to determine if there will be a statistical difference in the distribution of CNR values between the two systems. A lesion will be considered detectable if it meets the Rose criteria (i.e., CNR>3). A lesion observability (LO) may be defined as the percentage of the holes in the phantom that have a CNR greater than a given threshold value (based on the Rose criterion). For example, if the observability of the phantom is 50% with a threshold of 3, this means that 50% of the 48 holes of the phantom have a CNRmax that is greater than 3. Furthermore, by determining the observability as a function of acquisition time, the way in which the detectability of lesions increases with increasing acquisition time for PHC and CSA may be characterized. The dependency on the threshold value may be determined by repeating this procedure for a range of threshold values.

In some embodiments of the disclosed technology, the CSA is used for image acquisition and reconstruction. In some embodiments of the disclosed technology, the CSA allows gamma rays to reach the detector from all relevant angles, thereby increasing sensitivity, reducing effective radiation dose of MBI, and decreasing imaging time.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

The invention claimed is:

1. A breast imaging system, comprising:
a compressive sensing absorber (CSA) including a set of materials distributed in a medium to exhibit a random pattern of partial gamma ray absorption over different positions of the set of materials such that gamma ray emission from a breast traveling through the CSA is partially absorbed and is partially scattered by the random pattern to produce an output gamma ray radiation pattern having gamma rays in a range of different directions;
a gamma imaging device positioned relative to the CSA to collect gamma rays from the output gamma ray radiation pattern produced by the CSA to convert the collected gamma rays of the breast gamma ray emission from the breast into imaging signals representing an image of the breast; and
an imaging processing device coupled to receive image information of the imaging signals from the gamma imaging device and configured to reconstruct images in 2D or 3D based on a spatial distribution of the collected gamma rays from the breast.

2. The system of claim 1, wherein the set of materials distributed in the medium includes randomly distributed steel ball bearings within ballistic gel through which the gamma rays pass at different angles and originate at various depths in tissue of breast.

3. The system of claim 1, further comprising a radioactive point source structured to move through a predetermined image grid in front of the CSA and the gamma imaging device.

4. The system of claim 3, further comprising an XYZ plotter to move the radioactive point source within a 3D image grid.

5. The system of claim 4, wherein the XYZ plotter configured to, prior to imaging, determine a sensing matrix to be used for image reconstruction by moving the radioactive point source within the 3D image grid.

6. The system of claim 1, wherein the gamma rays are reconstructed using a discrete cosine transform (DCT).

7. An imaging system, comprising:
a radioactive point source configured to emit gamma ray photons;
a compressive sensing absorber (CSA) including randomly distributed materials within a medium through which gamma rays from the radioactive point source pass at different angles; and
a radiation detector structured to collect the gamma rays passing through the medium at different angles,
wherein the gamma rays passing through the medium at different angles is reconstructed using a discrete cosine transform (DCT).

8. The system of claim 7, wherein the materials are distributed within the medium such that gamma rays from the radioactive point source undergo partial absorption.

9. The system of claim 8, wherein the materials include steel ball bearings, and wherein the gamma rays from the radioactive point source scatter due to the steel ball bearings.

10. The system of claim 7, wherein the medium includes ballistic gel.

11. The system of claim 7, wherein sizes and distributions of the materials are determined based on at least one of image resolution, sensitivity, scatter or a probability of collecting independent measurements from a sample.

12. The system of claim 7, wherein the radioactive point source is structured to move through a predetermined image grid in front of the CSA.

13. The system of claim 12, further comprising an XYZ plotter to move the radioactive point source within a 3D image grid.

14. The system of claim 13, wherein the XYZ plotter configured to, prior to imaging, determine a sensing matrix to be used for image reconstruction by moving the radioactive point source within the 3D image grid.

15. A compressive sensing absorber (CSA) device, comprising:
a set of particles distributed with a predetermined random pattern in a medium such that gamma rays traveling through the medium are partially absorbed and scattered by the set of particles; and
a case configured to contain the medium and the set of particles and formed of a material that is transparent to gamma-ray radiation, wherein the case is configured to be attached to a gamma camera used for imaging.

16. The device of claim 15, wherein the set of particles distributed in the medium includes randomly distributed steel ball bearings within ballistic gel through which the gamma rays pass at different angles and originate at various depths in tissue.

17. The device of claim 15, wherein the medium containing the set of particles and a sensing matrix obtained by moving a gamma-ray radiation source within an image grid are used to collect compressive sensing measurements for imaging.

18. The device of claim 15, wherein sizes and distributions of the particles are determined based on at least one of image resolution, sensitivity, scatter or a probability of collecting independent measurements from a sample.

* * * * *